United States Patent [19]

Kiuchi et al.

[11] Patent Number: 5,083,447
[45] Date of Patent: Jan. 28, 1992

[54] WASHING MACHINE HAVING OPTICAL SENSOR FOR DETECTING LIGHT PERMEABILITY OF DETERGENT SOLUTION

[75] Inventors: Mitsuyuki Kiuchi, Nara; Hisayuki Imahashi; Shoichi Matsui, both of Kawanishi, Japan

[73] Assignee: Matsushita Electric Industrial Co., Ltd., Osaka, Japan

[21] Appl. No.: 471,610

[22] Filed: Jan. 29, 1990

[30] Foreign Application Priority Data

Jan. 27, 1989 [JP] Japan .................................. 1-17902
Mar. 17, 1989 [JP] Japan .................................. 1-67038
Jul. 31, 1989 [JP] Japan .................................. 1-198938

[51] Int. Cl.$^5$ .................................................. D06F 33/02
[52] U.S. Cl. .................................. 68/12.05; 68/12.02
[58] Field of Search ............ 68/12 R, 13 R, 12.02, 68/12.05, 12.27; 134/113; 356/436, 441, 442; 250/564, 565; 340/619

[56] References Cited

U.S. PATENT DOCUMENTS 4,222,250 9/1980 Torita ........................... 134/113 X
4,372,134 2/1983 Matsuo ............................. 68/12 R
4,653,294 3/1987 Akinaga ........................... 68/12 R

FOREIGN PATENT DOCUMENTS 0165990 8/1985 Japan ................................. 68/12 R
61-50595 3/1986 Japan .
0159997 7/1986 Japan .
61-159999 7/1986 Japan .
3317191 12/1988 Japan ................................. 68/12 R Primary Examiner—Philip R. Coe
Attorney, Agent, or Firm—Wenderoth, Lind & Ponack

[57] ABSTRACT

A washing machine includes an optical sensor for detecting a light permeability of detergent solution and rinse water in a washer tank. The optical sensor includes a light emitting element and a light receiving element. A microprocessor is provided for controlling a luminous intensity of the light emitted from the light emitting element. More specifically, the microprocessor sets the luminous intensity of the light emitting element such that an intensity of the light detected by the light receiving element is equal to or greater than a stored reference value during at least one of two operating states. The first of the two operating states is a state in which water is absent from the water tank. A second of the two operating states is a state in which water is present in the water tank and prior to agitation of the water in the water tank. Various processing cycles of the washing machine are carried out in accordance with the light permeability detected by the optical sensor.

5 Claims, 12 Drawing Sheets

WASHING MACHINE HAVING OPTICAL SENSOR FOR DETECTING LIGHT PERMEABILITY OF DETERGENT SOLUTION

BACKGROUND OF THE INVENTION

1. Field of the Invention

The present invention relates to a washing machine or laundry machine equipped with an optical sensor for detecting the light permeability of a detergent solution or rinse water in a washer tank.

2. Description of the Prior Art

A washing machine of the type referred to above, namely, a washing machine equipped with an optical sensor for detecting the light permeability of a solution of washing detergent, i.e., for detecting the amount of light that can penetrate the detergent solution, been disclosed in Japanese Patent Laid-open Publication No. 61-50595. More specifically, the washing machine of Tokkaisho 61-50595 is provided with an optical sensor comprised of light emitting and light receiving elements confronting each other in a washer tank, whereby the light permeability of the detergent solution in the washer tank is detected using an output of the light receiving element. A control circuit to which is generated an output of the optical sensor obtains data depicting the dirt content of the laundries on the basis of the time period consumed from the start of washing until the light permeability detected by the optical sensor decreases to a predetermined value (20% of the light permeability of clear water), and the washing machine is operated according to the dirt content data of the control circuit.

Meanwhile, a washing machine disclosed in Japanese Patent Laid-open Publication No. 61-159999 has been devised taking note of the fact that the light permeability detected by the optical sensor gradually increases after the start of washing, and thereafter it gradually decreases. A time point at the interface between the increase and decrease of the light permeability is set as an initial value of the data. In this washing machine, the type of detergent and the like are detected on the basis of both the time spent before the light permeability reaches the interface point after the start of washing, and the changing width of the light permeability.

In the washing machine disclosed in Japanese Patent Laid-open Publication No. 61-50595, however, if the light emitting surface of the light emitting element or the light receiving surface of the light receiving element is stained, the light intensity coming from the light emitting element to the light receiving element lessens to thereby diminish an output from the light receiving element. Accordingly, the light permeability detected by the optical sensor is a lower value than the actual value of the light permeability of the detergent in the washer tank. In consequence, the light permeability detected by the optical sensor reaches the predetermined value after the start of washing more quickly in comparison to the case where the elements are not stained. Therefore, the dirt content degree is erroneously detected. Particularly, since during use of the washing machine laundries and detergent are put in the washer tank, the light emitting and receiving elements provided in the washer tank are unavoidably stained. Moreover, the amount of the stain is generally increased in proportion to the usage time of the washing machine. As a result, the detecting accuracy of the optical sensor is deteriorates with time. Accordingly, the optical sensor cannot be relied upon for a long service in the detection of the dirt content of laundries.

Meanwhile, the change in the light permeability of the detergent solution in the washer tank is greatly influenced by the type of the detergent being used. Liquid detergent changes the light permeability significantly less than powdery detergent, and the light permeability of liquid detergent may not be reduced as to 20% of that of clear water. In such case, it is impossible to obtain the dirt content data. Therefore, the washing machine disclosed in Tokkaisho 61-50595 is not able to control washing operation in a manner which is responsive to the type of the detergent being used.

On the other hand, the washing machine disclosed in Tokkaisho 61-159999 is designed to detect the type of cleanser. However, according to the disclosed detecting method the type of the detergent can be detected only when the detergent is supplied into the tank before the water is added at the start of washing. In other words, if the detergent is put into the tank after the start of washing (after the start of stirring), the light permeability detected by the optical sensor declines after the start of washing. However, since the washing machine is arranged to operate based on the notion that the light permeability detected by the optical sensor increases at the start of washing and then, gradually decreases, the washing machine cannot detect the type of the detergent if the detergent is put into the tank after the start of washing. In addition, the change in the light permeability of the optical sensor is dependent not only on the type of detergent, but is also dependent on the amount of the detergent, and accordingly the light permeability detected by the optical sensor does not always follow a constant pattern of increasing once after the start of washing and thereafter decreasing.

SUMMARY OF THE INVENTION

A primary object of the present invention is to provide a washing machine which is arranged to detect the dirt content of the laundries with a high degree of accuracy, even when light emitting and light receiving elements of an optical sensor are stained.

A second object of the present invention is to provide a washing machine which is arranged to control washing and rinsing operation without being influenced by the staining on the optical sensor.

A third object of the present invention is to provide a washing machine which is arranged to control washing and rinsing operations using the data of the volume of laundries in a washer tank and the light permeability detected by an optical sensor.

A fourth object of the present invention is to provide a washing machine which is arranged to correctly detect the type of detergent in use without being influenced by the amount of the detergent used or the time the detergent is placed into the washer tank.

A fifth object of the present invention is to provide a washing machine which is arranged to control washing and rinsing operations in accordance with the type of detergent in use.

A sixth object of the present invention is to provide a washing machine which is arranged to control washing and rinsing operations on the basis of three data sets, namely data directed to the volume of laundries in a washer tank, the light permeability detected by an optical sensor and the type of detergent being used.

In accomplishing the above-described objects, a washing machine according to a first embodiment of the present invention is provided with an optical sensor comprised of a light emitting element and a light receiving element for detecting the light permeability of a detergent solution and rinse water in a washer tank, an output control unit for controlling an output generated from the light emitting element, and a storage unit. The control unit controls the light emitting element such that the light permeability of water or air in the washer tank becomes a reference value for the storage unit. In the washing machine, a reference value of the light permeability of supplied water is made different from that of air. An output of the light emitting element is controlled by the output control unit based on the reference value of the light permeability of the water or air, which is determined by a signal from a water level detecting unit.

Moreover, the above output control based on the reference value of supplied water is effected when the water level detecting unit detects the water as not being lower than a predetermined level. The data of outputs of the light emitting element or data of the light permeability when the optical sensor is set at the reference value is stored in the storage unit, which is utilized for a succeeding output control.

According to a second embodiment of the present invention, the washing machine is provided with an optical sensor comprised of a light emitting and light receiving elements for detecting the light permeability of a detergent solution and rinse water in a washer tank, an output control unit for controlling an output from the light emitting element, a storage device, and a control unit for controlling washing and rinsing operations. The output control unit controls the light emitting element such that the light permeability of water or air fed into the washer tank becomes a reference value, to thereby initialize the optical sensor. Moreover, the control unit controls the washing or rinsing operation based on the change of the light permeability indicated by the optical sensor. The output control is carried out during the supply of clear water. The washing operation is controlled by the saturating time from the start of washing until the light permeability of the optical sensor becomes approximately constant, and the changing width of the light permeability of the optical sensor, so that an additional washing time from the saturating time point is arranged on the basis of the changing width of the light permeability.

According to a third embodiment, the washing machine is provided with an optical sensor comprised of a light emitting and light receiving elements for detecting the light permeability of a detergent solution and rinse water in a washer tank, a storage device, a control unit for controlling washing and rinsing operations, and a volume sensor for detecting the volume of laundries in the washer tank. The control unit controls the washing or rinsing operation based on the data of the volume sensor and the changing width of the light permeability of the optical sensor indicated during washing or rinsing operation. Moreover, according to this embodiment, the control unit sets the upper and lower limits of the washing time from the volume of laundries detected by the volume sensor.

According to a fourth embodiment of the present invention, the washing machine is provided with an optical sensor comprised of a light emitting and a light receiving elements for detecting the light permeability of a detergent solution and rinse water in a washer tank, and a judging unit for judging the detergent. The judging unit judges whether liquid detergent or powdery detergent is used through comparison of a reference light permeability of the optical sensor which is based on the light permeability of water or air fed into the washer tank with the light permeability of the optical sensor shown during the washing operation.

According to a fifth embodiment of the present invention, the washing machine is provided with an optical sensor comprised of a light emitting and a light receiving elements for detecting the light permeability of a detergent solution and rinse water in a washer tank, a judging unit for judging a detergent type, and a control unit for controlling washing and rinsing operations. The judging unit judges the kind of detergent type, i.e., liquid or powder, through comparison of a reference light permeability of the optical sensor with the light permeability indicated during the washing operation, whereby the control unit controls washing or rinsing operation in accordance with the judged detergent type.

According to a sixth embodiment of the present invention, the washing machine is provided with an optical sensor comprised of a light emitting and a light receiving elements for detecting the light permeability of a detergent solution and rinse water in a washer tank, a volume sensor for detecting the volume of laundries in the washer tank, a judging unit for judging the detergent type, and a control unit for controlling washing and rinsing operations. The control unit controls the washing or rinsing operation based on the data of the laundry volume detected by the volume sensor and the detergent type judged by the judging unit.

In the washing machine of the first embodiment of the invention, an output of the light emitting element is controlled based on a reference value of the light permeability of water or air which has a high light permeability, to initialize the optical sensor. Consequently, the dirt content of the laundries is detected by the relative change of the light permeability from that of water or air, without being influenced by stains at a drainage path in which the optical sensor is provided, thus accomplishing an accurate detection of dirt content.

Moreover, since the light permeability of water is different from that of air, the reference value is changed between water and air, so that the initial setting of the optical sensor is enabled both in the case of water and in the case of air. Further, if the water level detecting device detects no water, the light emitting element of the optical sensor is controlled on the basis of the reference value of air. On the contrary, if water is detected by the detecting device, the light emitting element is controlled on the basis of the reference value of water. Moreover, the light emitting element is controlled during a previous supplying time of rinse water such that an output signal of the optical sensor becomes a set value, and this controlling data is stored. Therefore, at the coming start of washing, the light emitting element is so controlled by the stored controlling data as to generate an output of a fixed value, to thereby detect the change of data after washing and stirring. In the case where only the air is present in the washer tank before the start of washing, since it is feared that the optical axis of each element of the optical sensor may be deviated because of the adhesion of water drops, an output of the light emitting element is controlled relatively larger as compared in the case where there is clear water in the tank.

Although the output signal from the optical sensor becomes a Hi level and may exceed beyond the dynamic range when the water is actually fed in the tank, the data stored in the storage device is useful to solve such problem. Therefore, the change of the output signal due to the real dirt content can be detected.

Further, in the second embodiment of the present invention, the light permeability is detected by the optical sensor after the sensor is initialized, so as to control the washing or rinsing operation. Accordingly, the optical sensor positively works for a long period of time without being affected by staining. Moreover, the optical sensor is initialized during the supply of rinse water, the light permeability of the clear water can be used as a reference value. Since washing is controlled by the saturating time spent before the saturating time point of the change of the optical sensor and by the changing width of the output of the optical sensor, the quality of stains related to the saturating time and the volume of stains related to the output changing ratio of the optical sensor can be detected, to thereby facilitate an optimum control of washing and rinsing operations.

In the washing machine according to the third embodiment of the present invention, washing by detergent solution or by clear water can be controlled in consideration not only of the dirt content of the laundries shown by the optical sensor, but also in consideration of the laundry volume in the washer tank. Therefore, the washing machine can operate in the similar manner as if it were by a user's own control.

According to the fourth embodiment of the present invention, taking note of the fact that the type of a detergent can be known through comparison of the light permeability after the start of washing with that when the water is not supplied, that is, the light permeability of air as a reference, in the case where liquid detergent is used, for example, the light permeability after the start of washing is reduced to approximately 80% based on the reference light permeability of the air, while, in the case of powdery detergent, the light permeability after the start of washing is decreased to about 40-60%. Therefore, this conspicuous change of the light permeability enables the judgement as to the type of the detergent.

Since the change of the output from the optical sensor is detected while rinse water is being supplied, namely, based on the light permeability of clear water, the relative change of the output is approximately equivalent to the change corresponding to the absolute volume of dirt content, and therefore it becomes possible to detect the volume of dirt content. In the case of powdery detergent, the output change of the optical sensor caused only by the dirt content of the detergent solution is approximately 50% and accordingly, the change thereafter, i.e., over 50% corresponds to the amount or degree of dirt. In other words, it becomes possible to detect the presence of the detergent and the dirt content thereof by the present embodiment.

According to the fifth embodiment of the present invention, since washing is arranged to be controlled in accordance with the detergent type, and data of types which greatly affect the detection by the optical sensor is added, washing or rinsing control with high accuracy can be realized.

According to the sixth embodiment of the present invention, since the data of detergents types and the data of volume of the laundries are added to the dirtiness data obtained by the optical sensor, washing can be performed under more accurate control.

BRIEF DESCRIPTION OF THE DRAWINGS

These and other objects and features of the present invention will become apparent from the following description taken in conjunction with preferred embodiments thereof with reference to the accompanying drawings in which throughout like parts are designated by like reference numerals and in which.

DESCRIPTION OF PREFERRED EMBODIMENTS

Referring to FIGS. 1-6, the structure of an automatic washing machine according to one preferred embodiment of the present invention will be described.

Figure 6:
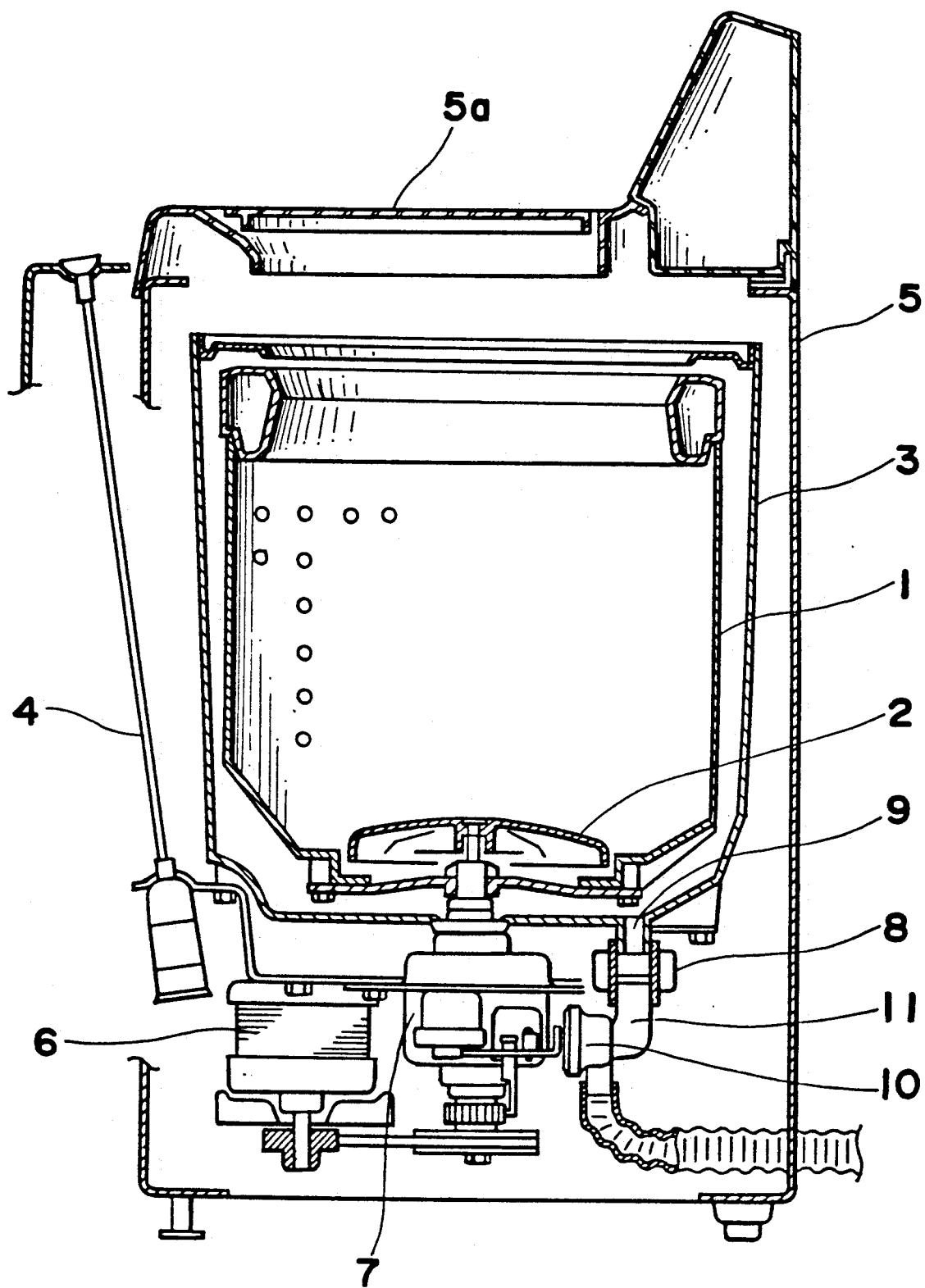
FIG. 6 is a cross sectional view of the washing machine.

The washing machine shown in FIG. 6 is provided with a washer tank 1 which serves also as a dryer tank (hereinafter referred to as a washer tank). A stirring vane 2 is rotatively placed in the bottom section inside the washer tank 1. A water reservoir 3 housing the washer tank 1 is supported by a main body 5 of the washing machine through a suspension 4, so that the water reservoir 3 is restricted from vibrating. A lid 5a which is freely openable and closable is provided in the upper portion of the main body 5. There is a motor 6 below the water reservoir 3, the rotation of which is transmitted to the stirring vane 2 through a transmission mechanism 7. At the time of drying, the transmission mechanism 7 also transmits the rotating force of the motor 6 to the washer tank 1. Further, a water exit 9 formed in the bottom portion of the water reservoir 3 is communicated to a drain valve 10 through a drainage path 11. A light emitting and receiving unit 8 comprised of a light emitting element and a light receiving element is installed in a part of the drainage path 11.

Referring to a block diagram of FIG. 2, the circuit construction of the washing machine will be described hereinbelow.

Figure 2:
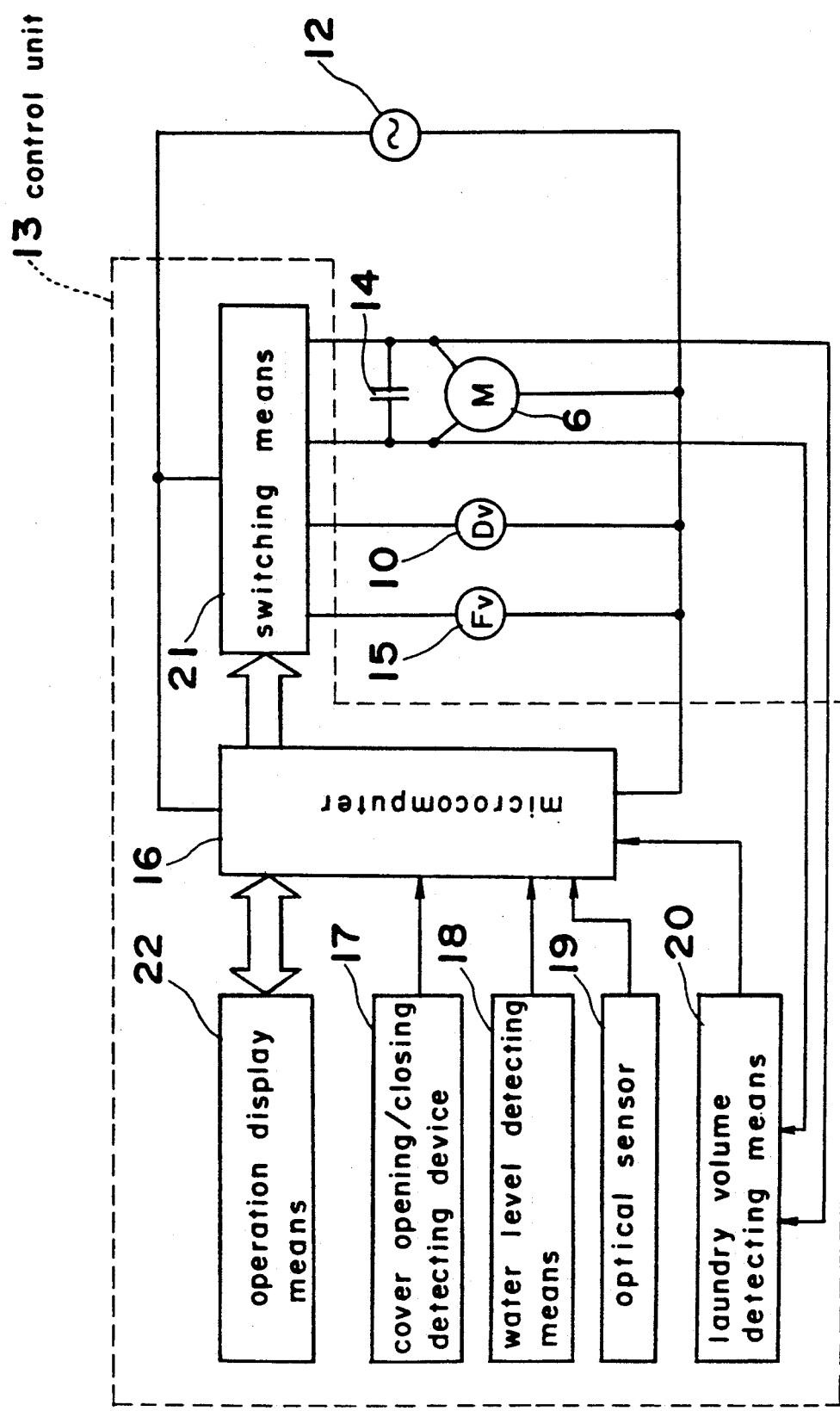
FIG. 2 is a block diagram showing the circuit structure of the washing machine of FIG. 1.

In FIG. 2, an alternating current source 12 supplies power to a control unit 13, the motor 6 provided with a phase advancing capacitor 14, the drain valve 10 and a feed valve 15. The control unit 13 has a microcomputer 16 which is the center of the controlling operations. At an input of the microcomputer 16 are connected a cover opening/closing detecting device 17 which detects whether the lid 5a is opened or closed, a water level detecting device 18 for detecting the water level within the washer tank 1, an optical sensor 19 including the light emitting and receiving unit 8 which detects the light permeability of a detergent solution and rinse water in the washer tank 1, and a volume detecting device 20 for detecting the volume of laundries in the washer tank 1 using the change of a terminal voltage of the capacitor 14 when the motor 6 is turned off. The volume detecting device 20 counts the number of pulses of the capacitor 4 when the motor 6 is controlled in the normal or reverse rotation thereof or the motor 6 is turned off, and determine that there are a relatively large amount of laundries in the washer tank when the number of pulses is small. On the other hand, at an output side of the microcomputer 16 is connected a switching device 21 which controls the load of the motor 6 and the like in response to an output signal from the microcomputer. Moreover, the microcomputer 16 is further connected with an operation display device 22 for transmitting and receiving signals therewith.

The above-mentioned control unit 13 will operate in the following manner.

In the first place, when the microcomputer 16 receives a start signal from the operation display device 22, the microcomputer carries out the programmed operation processes that is, washing using a detergent solution, rinsing using clear water and drying. More specifically, when the water is supplied in the washing process, the microcomputer 16 controls the feed valve 15 to be opened and the drain valve 10 to be closed through the switching device 21. In the middle of the supply of water, when the water level is low, the motor 6 is driven to rotate the stirring vane 2 for a predetermined time. Immediately after the rotation of the motor 6 is stopped, the microcomputer 16 reads a signal from the volume detecting device 20 so as to determine the volume of the laundries from the attenuating change of the terminal voltage of the capacitor of the motor 6. Consequently, a water stream, washing time, rinsing time, drying time, etc., which are appropriate for the detected volume of laundries are determined, and each process is carried out.

Figure 1:
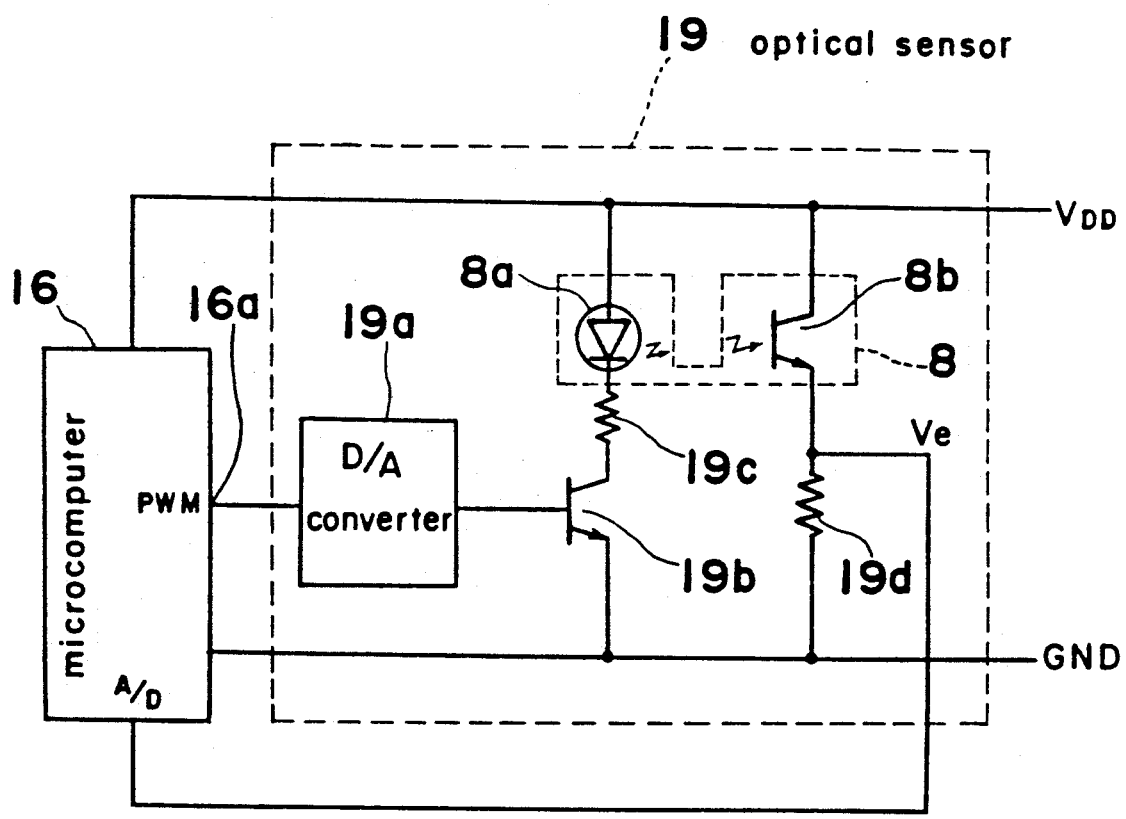
FIG. 1 is a circuit diagram of an optical sensor of a washing machine according to one embodiment of the present invention.

Referring now to FIG. 1, the specific structure of the optical sensor 19 which is a main feature of the present invention will be explained.

The microcomputer 16 is provided with a PWM output terminal 16a which freely controls an output pulse width. An output pulse from the PWM output terminal 16a is, via a D/A converter 19a, inputted to a base of a transistor 19b. In other words, an anode current in a light emitting diode 8a which is a light emitting element of the light emitting and receiving unit 8 and connected to a collector of the transistor 19b is controlled in accordance with the pulse width. The D/A converter 19a and transistor 19b constitute a current variable means for the light emitting element. A phototransistor 8b which is a light receiving element for receiving light from the light emitting diode 8a has an emitter connected to a resistor 19d, and an output signal $V_e$ (light permeability) of the phototransistor 8b can be output as a voltage. This output signal Ve is connected to an A/D input terminal of the microcomputer 16 to be A/D converted.

The microcomputer 16 controls the optical sensor 19 as follows.

Figure 3:
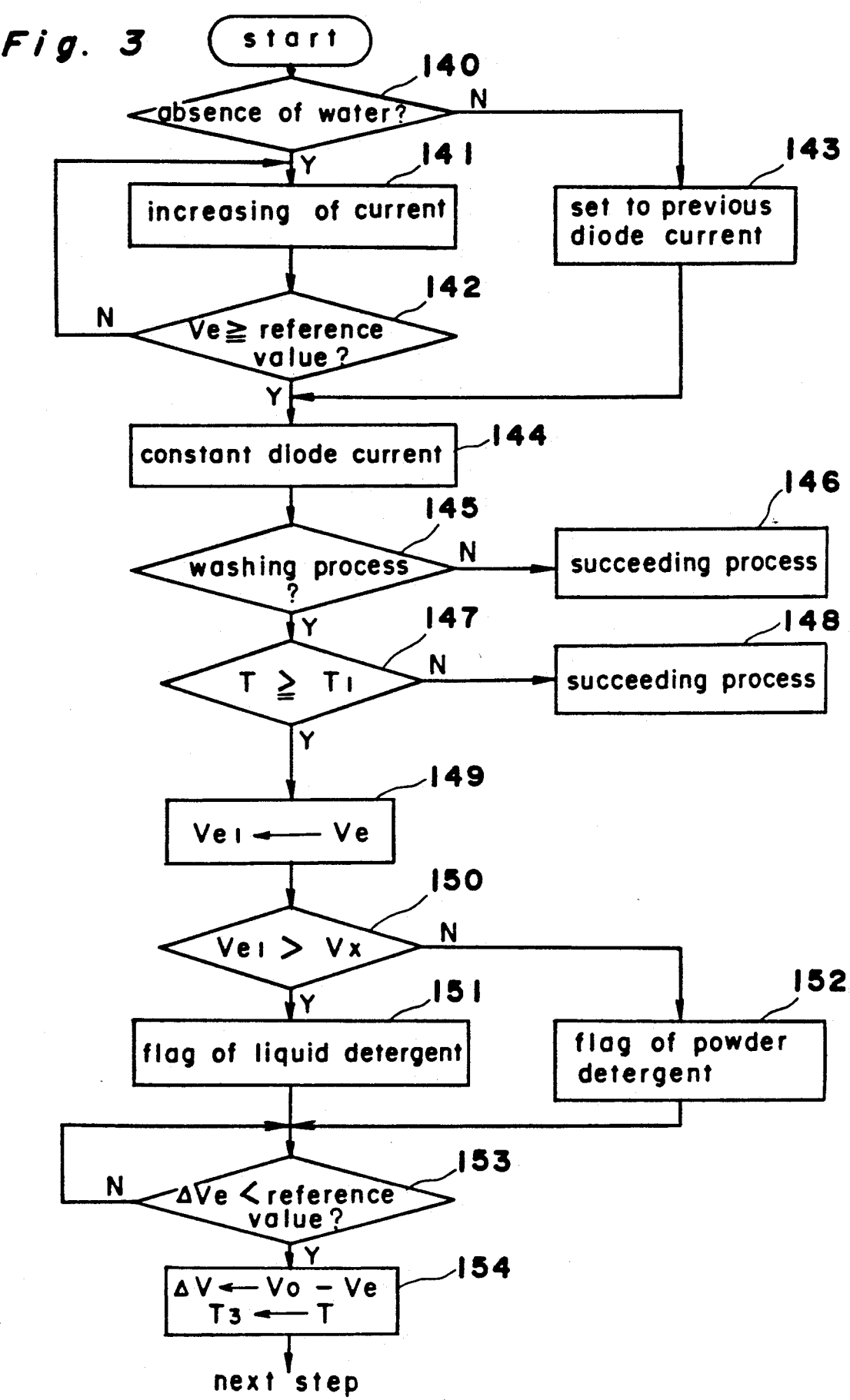
FIG. 3 is a flow-chart showing the controlling operation of the washing machine of FIG. 1.
Figures 4, 5:
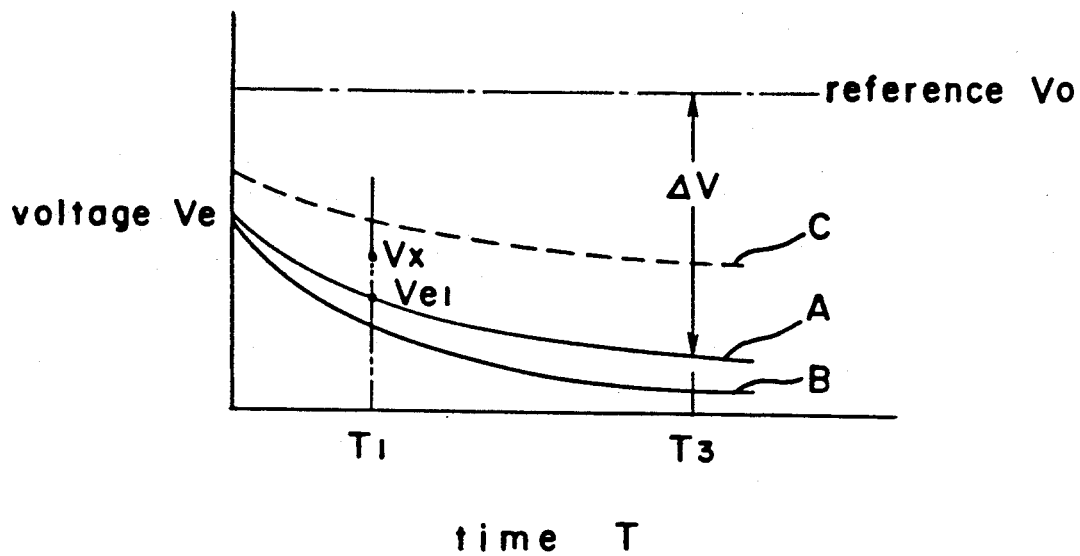
FIG. 4 is a graph showing the change of an output of the optical sensor of FIG. 1.
FIG. 5 is a table showing judging contents in the controlling operation of the washing machine of FIG. 1.

Referring to a flow chart of FIG. 3, the water level detecting device 18 detects the presence or absence of water in the washer tank 1 in step 140. Without water, the current of the light emitting diode 8a is increased in step 141 and, the optical sensor is initialized such that the output voltage Ve of the phototransistor 8b becomes a reference value Vo in step 142. That is to say, the light permeability of air is set as a reference value. The pulse width from the PWM output terminal 16a should be increased when the current of the light emitting diode 8a is to be increased. Because of this initial setting of the optical sensor, a decrease in the detecting accuracy due to the decline of the output voltage of the phototransistor 8b resulting from the staining of the surface of the light emitting diode 8a or phototransistor 8b can be prevented. In the case where the water is already supplied in the washer tank 1, the optical sensor is set with the current of the light emitting diode 8a employed in the previous operation, in step 143. Then, in step 144, a constant current is fed to the light emitting diode 8a. It is detected in step 145 whether the washing process is selected. In the event that the washing process is not selected, the flow proceeds to a succeeding process in step 146 (for example, rinsing process). In the washing process, if there is no water in the tank 1, the volume detecting device 20 detects the volume of laundries, and the water is fed to a predetermined water level, and thereafter the stirring vane 2 is rotated to produce the water stream. The change in the output voltage Ve of the phototransistor 8b after the start of stirring is indicated in the graph of FIG. 4 in which lines A and B show the voltage Ve change when a powder detergent is used, and a line C indicates the change when a liquid detergent is used. If washing is completed before a time point T1 (e.g., the user sets the washing time period shorter than T1), the operation flow advances to a next process (steps 147 and 148). In step 149, the output voltage Ve is set to be Ve1 at the time point T1 after the start of washing. In step 150, it is judged whether Ve1 is larger than the judging value Vx set for judging the type of detergent. If Ve1 > Vx holds (in the case shown by line C in FIG. 4), a flag denoting liquid detergent is set in step 151. Or, if Ve1 ≦ Vx holds (in the case shown by lines A and B in FIG. 4), a flag denoting powder detergent is set up in step 152. Since the light permeability of the liquid detergent is decreased to 80% in comparison with the reference value Vo, which is the light permeability when no water is present in the washer tank, namely, the light permeability of the air, while the light permeability of powder detergent is lowered to 40-60%, Vx is set to be at about the middle of the light permeability between the liquid and powder detergents, to thereby enable the detection of the detergent type. The changing ratio ΔVe of the output voltage Ve is detected in step 153. It is regarded as a saturating point of the light permeability when ΔVe is smaller than a set value. A difference of ΔV between the reference value Vo of the light permeability of air and the output voltage Ve1 is obtained in step 154. The time to the saturating point is T3.

With reference to a table of FIG. 5, how the difference ΔV and the time T3 are utilized for the control of washing will be described.

In FIG. 5, the difference ΔV and the time T3 are classified into three groups, respectively, large, middle and small. By way of example, when both ΔV and T3 are small, the washing time is shortened, whereas, when both ΔV and T3 are in the middle group, the washing time is ordinary (middle). In the manner as above, data on the difference ΔV and time T3 is fuzzy-controlled for washing.

Furthermore, according to the present invention, washing can be controlled by three data sets, i.e., volume data of laundries detected by the volume detecting device 20 in addition to the data of ΔV and T3, which will be described hereinbelow.

In other words, the judging result from ΔV and T3 is classified into three groups, namely, large, middle and small. By comparing the result with the washing time determined by the volume of laundries detected by the detecting device 20, the washing time is controlled 3 minutes longer in the event that the result is large. If the result is middle, the washing time is maintained as it is. On the other hand, if the result is small, the washing time is shortened by two minutes. Thus, washing can be controlled in an optimum manner. If the washing time is determined from the total point of view based on the detected volume of the laundries W1 and the dirt content W2 (determined by ΔV and T3), washing can be controlled as if it were done by the user himself or herself, with the volume and dirt content of laundries taken into consideration as when the user selects the washing time.

Although the foregoing description is related to the detecting of the dirt content and to the controlling operation therefor in the washing process, the same also holds true in the rinsing process.

Since ΔV changes in accordance with the detergent type as shown in FIG. 4, the value ΔV classified in the groups, large, middle and small in FIG. 5 may be changed corresponding to the detergent type. Moreover, the detecting accuracy of the saturating point of dirt may be rendered variable corresponding to the type of detergent.

In the foregoing embodiment, since the optical sensor is set at the initial stage when the clear air is in the washer tank, the detection of dirt is based on the relative change of the light permeability from that of air, and accordingly the detection is free from influences of stains in the drainage path where the optical sensor is installed or the stains interfering with the light detection of the optical sensor, thereby realizing an accurate detection of dirt.

In addition, since it is possible to detect the detergent type by the relative change of the output of the optical sensor between the time when the air is in the washer tank and after the start of washing, the data of the detergent type can be utilized for an accurate detection of dirt and accordingly for an accurate control of washing.

Hereinafter, an optical sensor and its control circuit of a washing machine according to a modified embodiment of the present invention will be explained with reference to FIG. 7.

Figure 7:
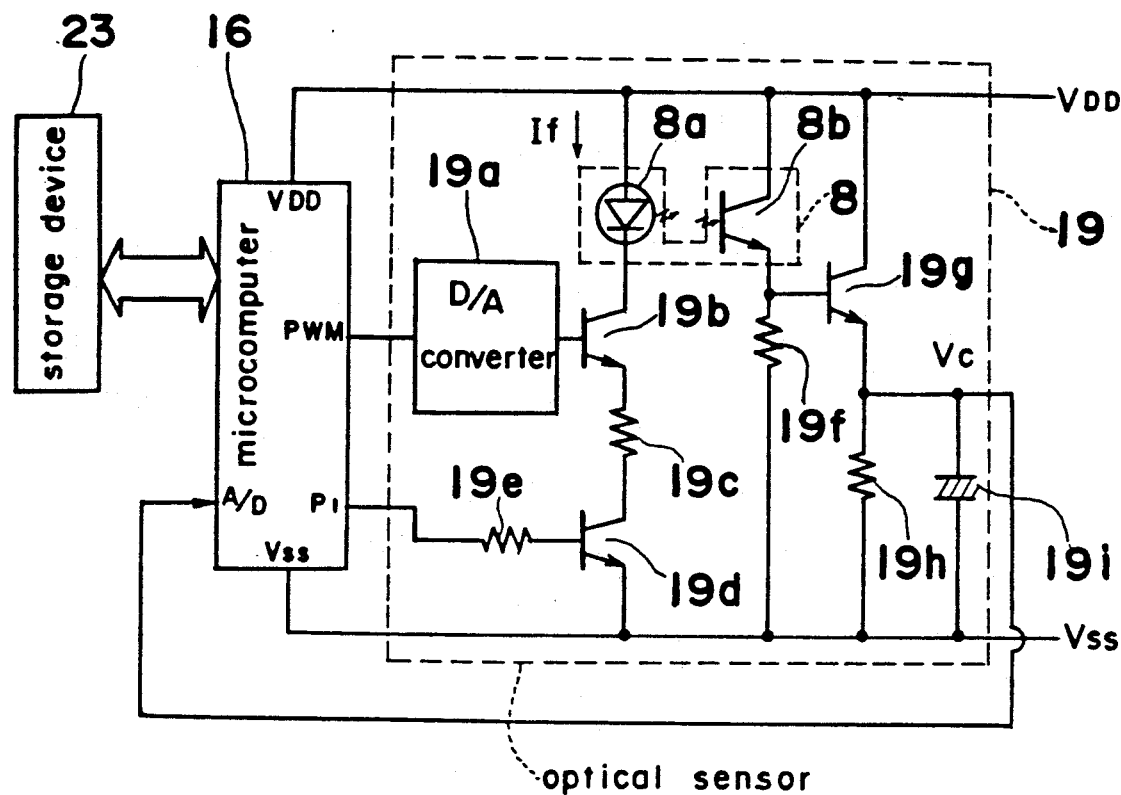
FIG. 7 is a circuit diagram of an optical sensor of a washing machine according to a modified embodiment of the present invention.

In FIG. 7, a pulse width controlling circuit (referred to a PWM circuit hereinafter) for controlling the current of the light emitting diode 8a in the light emitting and receiving unit 8, and an A/D converter for converting an analog signal to a digital signal is built in the microcomputer 16. A storage device 23 stores a control signal for controlling the current of the light emitting diode 8a (output controlling signal), namely, it stores data of PWM signals. This storage device 23 uses, for example, a non-volatile memory. The PWM signal from the microcomputer 16 is added to the D/A converter 19a (generally, an integrating circuit) to be converted to a direct current voltage to thereby control the voltage at the base of the transistor 19b. The collector of the transistor 19b is connected to the light emitting diode 8a, and the emitter thereof is connected to an emitter resistor 19c, thereby constituting a constant current circuit able to control the current of the light emitting diode 8a responsive to the base voltage. A switching transistor 19e is connected in series to the emitter resistor 19c, so that the current of the light emitting diode 8a is controlled on and off and pulse-driven by an output signal P1 of the microcomputer 16. A load resistor 19f of the phototransistor 8b, an emitter follower circuit of a transistor 19g, a resistor 19h and a capacitor 19i form a peak hold circuit so as to stabilize an output signal of the pulse-driven light emitting and receiving unit 8, thus reducing errors in A/D conversion.

Figure 8:
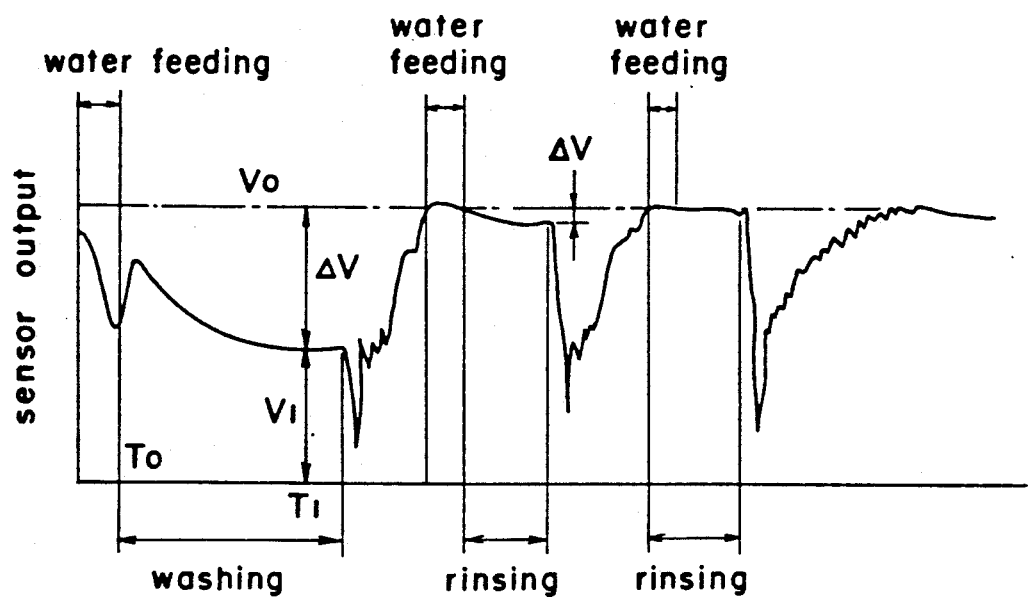
FIG. 8 is a graph showing an output of the optical sensor of FIG. 7.

The change of an output of the optical sensor 19 in the entire process of operation is indicated in the graph of FIG. 8. In this case, the change denotes a change after the current of the light emitting diode 8a is controlled to generate a preset output. As is clear from FIG. 8, the light permeability during washing is detected by the change of the output of the optical sensor from the reference value Vo which is set when the rinse water is supplied (the light permeability is represented by ΔV/Vo×100% wherein ΔV indicates the difference between the output V1 and reference output Vo). The light permeability expresses the dirt content and cleanliness of the laundries. Also, the change of the output from the clear water at the time of rinsing is seen from FIG. 8.

Figure 9:
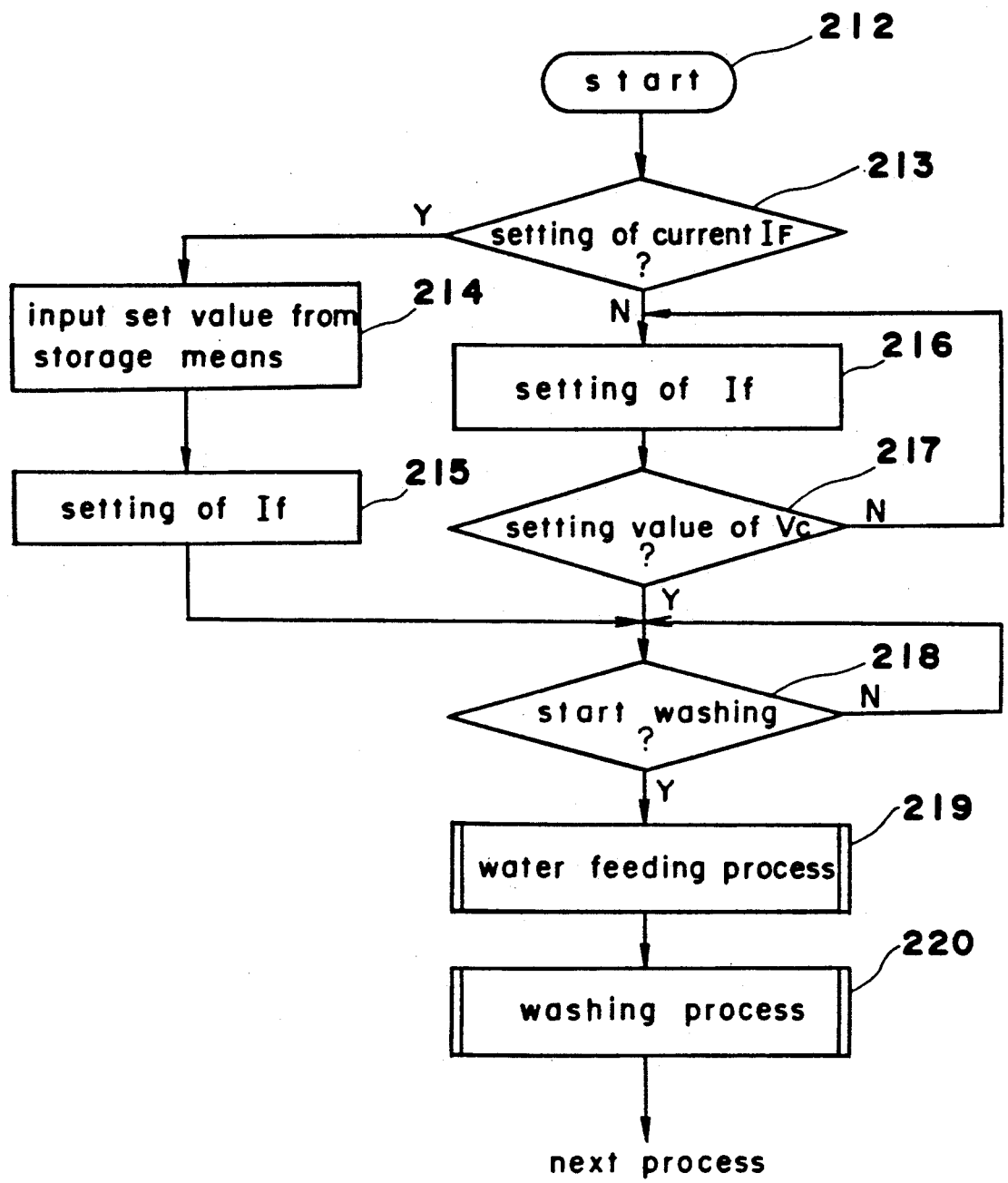
FIG. 9 is a flow chart showing the setting of the optical sensor at the start of washing.

FIG. 9 is a flow chart showing how the optical sensor is set at the start of washing. Upon supply of the power in step 212, it is detected in step 213 whether or not the current I$_F$ of the light emitting diode 8a is set. If I$_F$ is set, the set value is inputted from the storage device (memory) 23 in step 214, and the microcomputer 16 sets If by the PWM signals based on the inputted data in step 215. If I$_F$ is not set in step 213, it is adjusted in step 216, and the PWM signal is controlled such that the output signal Vc of the optical sensor 19 is a set value, thereby controlling the output of the D/A converter circuit 19a of FIG. 7. The data read out from the storage device 23 is the data set at the previous rinsing time.

Figure 10:
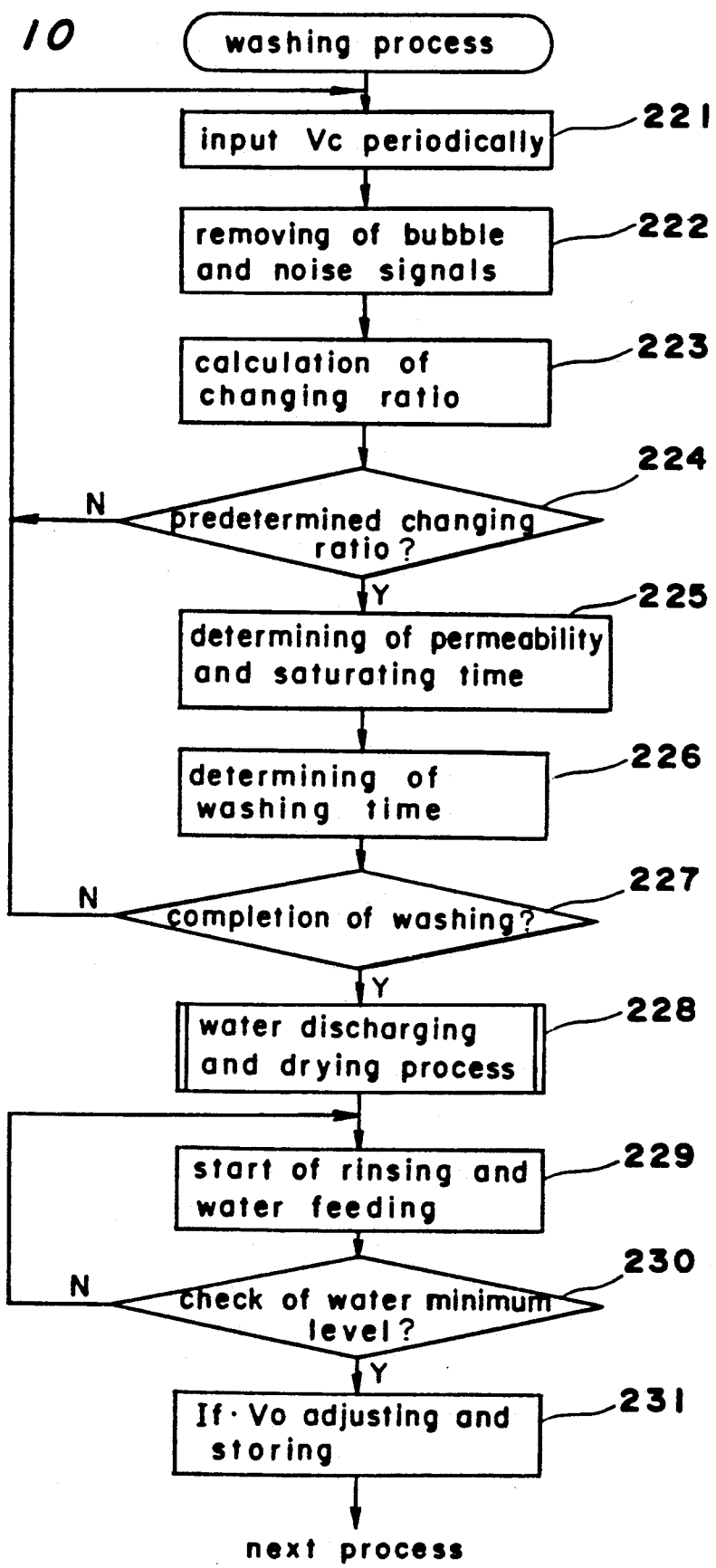
FIG. 10 is a flow chart showing the change detecting operation of the optical sensor.

The detecting flow of the change of the output of the optical sensor 19 during the washing process is indicated in FIG. 10.

The light emitting diode 8a is pulse-driven at a set level periodically in step 221 to input data of outputs Vc of the optical sensor 19. Since the output data includes bubbles and noise components, such data at an extraordinarily low level is removed, and only signals of a suitable level are taken out in step 222. The changing ratio of the data Vc is obtained in step 223, and judged in step 224 whether it is a predetermined ratio. The light permeability when the changing ratio, becomes a predetermined ratio and the saturating time are stored in step 225 to determine the washing time in step 226. When the determined washing time has passed, washing is completed in step 227. Then, discharging of water and drying are carried out in step 228. After it is detected in step 229 whether the rinse water is filled in the tank, the current of the light emitting diode 8a is controlled such that the output signal Vc of the optical sensor 19 shows the reference value Vo.

Figure 11:
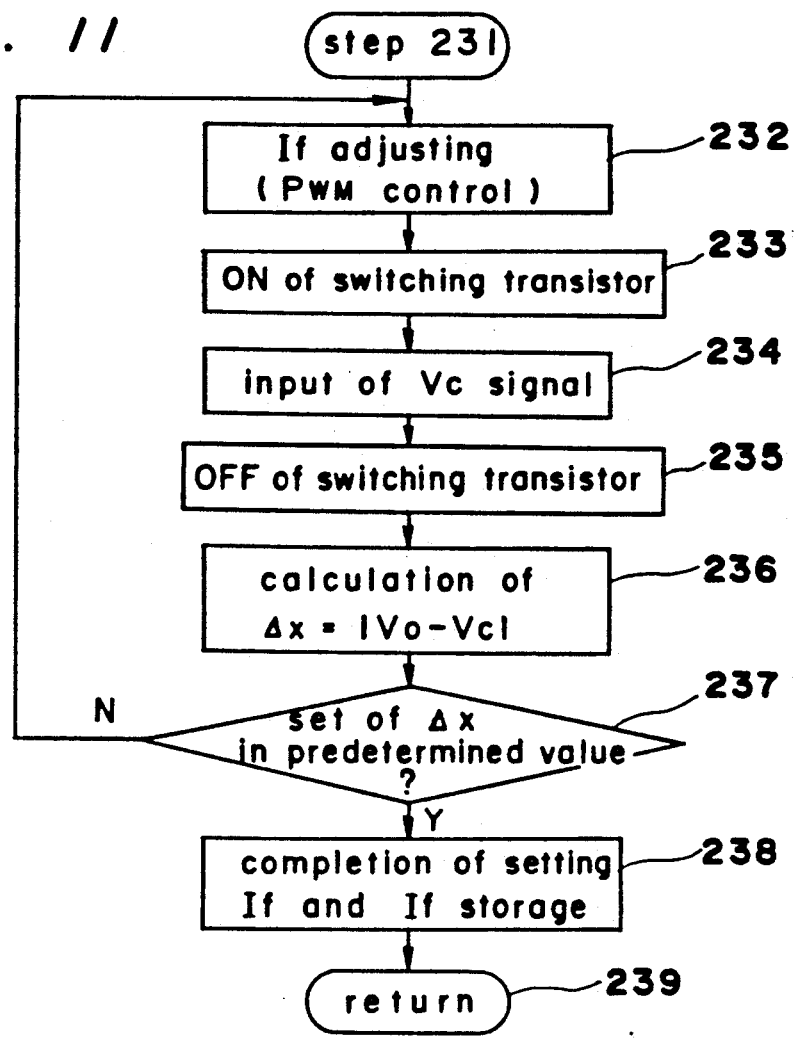
FIG. 11 is a flow chart of a subroutine for setting and storing an output of the optical sensor to a reference value.

A flow chart of FIG. 11 explains the controlling process when the output signal of the optical sensor is set to be the reference value Vo.

In step 232, the current If of the light emitting diode 8a is controlled. In step 233, the switching transistor is turned on to input the signal Vc of the optical sensor 19 into the microcomputer 16 for A/D conversion. Then, the switching transistor 19d is turned off in step 235. A difference $\Delta X$ between the reference value Vo and the input signal Vc is calculated in step 236. In step 237, PWM control is performed such that the difference $\Delta X$ is within a predetermined value. If the difference is within the predetermined value, the output controlling data is stored in the storage means 23, and the optical sensor 19 is fixed by the stored data thereafter turning on and off the current of the light emitting diode 8a.

In the above-described embodiment, the output voltage of the optical sensor is set at the reference value at the supplying time of the rinse water, so that the dirt content or cleanliness of the laundries is detected by the change of the output voltage from the reference value. In general, the water supplied as rinse water has 100% light permeability. Therefore, the light permeability or dirt content of the water can be detected by the changing ratio of the output voltage of the optical sensor with respect to the reference value. Particularly, for detecting the dirt content of the laundries at the time of washing, the change of the light permeability from the clear water will carry out the detection.

Further, since the previous reference value is arranged to be stored in the storage device 23, it may be useful during case where washing is continuously performed subsequent to the previous one (in the case where water drops are still adhered to the optical sensor 19 because of the previous washing, resulting in an erroneous detection). Accordingly, no complicated control is required even in the continuous washing.

Figure 12:
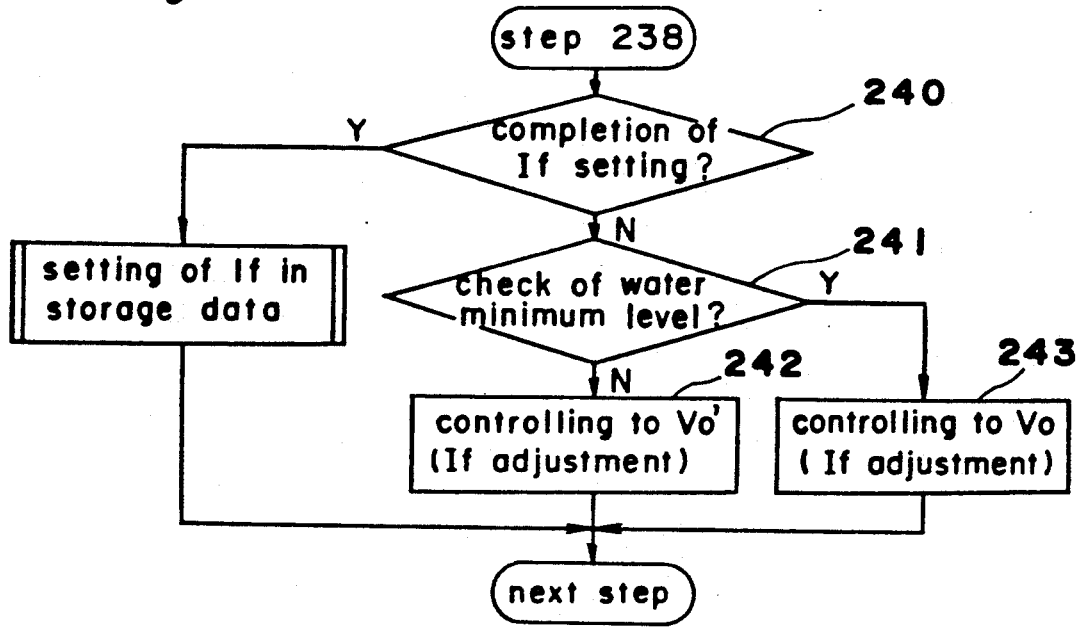
FIG. 12 is a flow chart showing the controlling operation of the optical sensor before washing.

The controlling process without the output controlling data will be described with reference to FIG. 12.

In the event that the output controlling data is not found in step 240, or the data is found to be inappropriate, the presence or absence of water is detected in step 241. If the water is found to be above the minimum water level in step 241, that is, if there is some water in the washer tank, the output voltage of the optical sensor is set at the reference value Vo in step 243. On the contrary, if there is no water in the washer tank, the output voltage is set to a second reference value Vo'. This is because the refractive index is different for air and water. Since the reference value Vo for the clear water is 1.1 times larger in comparison with the reference value Vo' for air, Vo' is set smaller than Vo.

Figure 13:
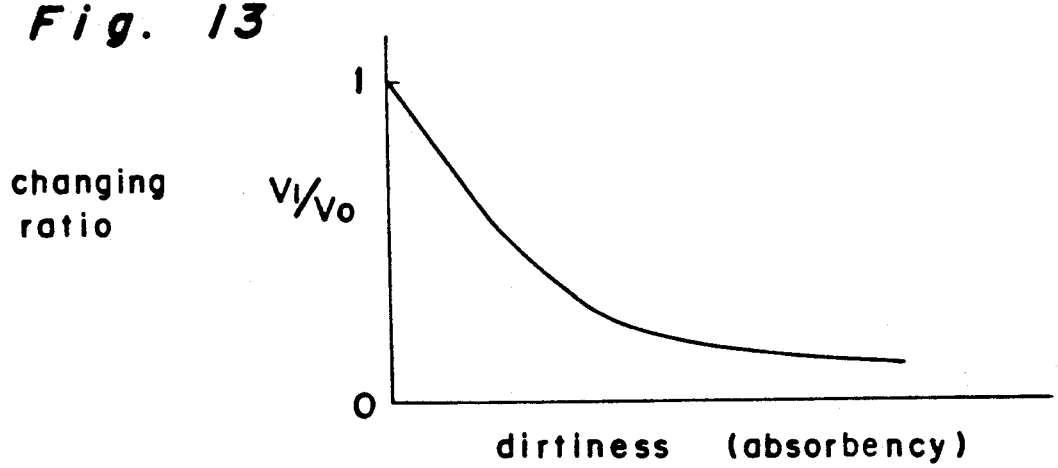
FIG. 13 is a graph showing the relation between the dirt content degree and the changing ratio of an optical sensor output V1 with respect to an optical sensor output Vo during the supply of water.

With reference to FIG. 13, the basic principle of the detection of dirt content and cleanliness will be described.

Specifically, when the output from the light emitting diode 8a is made constant, the ratio between the generated light amount Io and the penetrating light amount I1 when the water is clear water is represented by $I1/Io = e^{-k1 \cdot l}$, wherein k1 is a light absorbing factor and l is an optical path length. Similarly, when the water is dirty, the ratio between the generated light amount Io and the penetrating light amount I2 is indicated by $I2/Io = e^{-k2 \cdot l}$, wherein k2 represents a light absorbing factor of the dirty liquid. If Io is constant, the following equation is held;

$$I2/I1 = e^{-(k2-k1)l}$$

Figure 14:
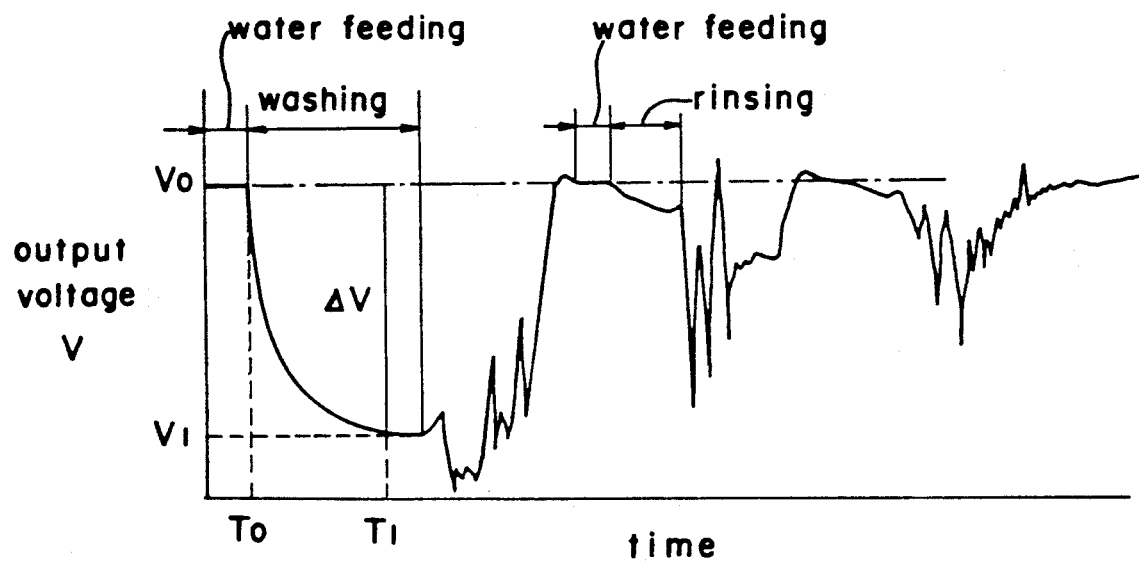
FIG. 14 is a timing chart of an output signal of the optical sensor from the start of washing to drying.

Since the penetrating light amount I1 when the water is clear is proportional to Vo shown in FIG. 14, and the penetrating light amount I2 when the water is dirty is proportional to V1 of FIG. 14, an equation;

$$V1/Vo = e^{-(k2-k1)l}$$

is obtained. Accordingly, it is understood that the changing ratio V1/Vo of the sensor output for the voltage Vo when the rinse water is supplied is changed logarithmically to the change of dirt content (the change of the light absorbing factor), as viewed from the graph of FIG. 13. In other words, $$\ln(V1-Vo) = -\Delta k \cdot l \quad (\Delta k = k2 - k1)$$

Therefore, it is so determined that the larger the changing ratio is, the greater the dirt content is, thus increasing the washing time, or strengthening the stirring force.

Although the current of the light emitting diode 8a is controlled through D/A conversion by the PWM controlling and integrating circuit in the foregoing embodiment, it may be effected by direct D/A conversion. Moreover, in setting the optical sensor at the reference voltage Vo, although it is easy if the current of the light emitting diode 8a is increased from 0, it takes much time. In addition, since the output control requires a good responding capability, the capacity of the capacitor 19i should be rendered small.

Figure 15:
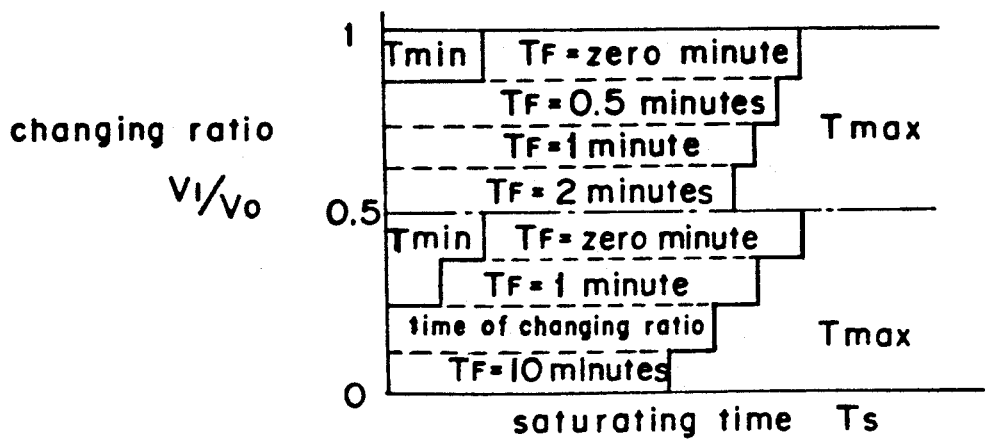
FIG. 15 is a graph showing the controlling contents for the washing time.

The washing time can also be controlled also in the other modification of the present invention, which will be described with reference to FIG. 15.

The washing time TW is expressed by TW=TS+TF (wherein TS is a saturating time until the change of the output of the optical sensor becomes constant after the start of washing, and TF is the time corresponding to the changing ratio V1/Vo (Vo being the reference value and V1 being the output of the optical sensor at the saturating time point)). In considering the case where the light permeability does not reach the saturating point, a minimum value Tmin and a maximum value Tmax are set for the washing time, which are changed corresponding to the volume of the laundries. Therefore, when a relatively large amount of laundries are to be washed, Tmin and Tmax are large. The changing ratio V1/Vo is different for liquid detergent and powder detergent, that is, not smaller than 0.5 and smaller than 0.5, respectively. When the powder detergent is used for lightly soiled laundries, V1/Vo is approximately 0.5. As the dirtiness of the laundries increases, the changing ratio becomes smaller than 0.5. On the other hand, when the liquid detergent is used, if the laundries are a little dirty, V1/Vo becomes closer to 1, and it becomes smaller than 1 as the dirtiness increases. Since the logarithmic value of V1/Vo is inversely proportional to the dirt content, the laundries are much dirtier as the changing ratio V1/Vo becomes smaller.

TF should be increased logarithmically in order to increase the washing time.

Figure 16:
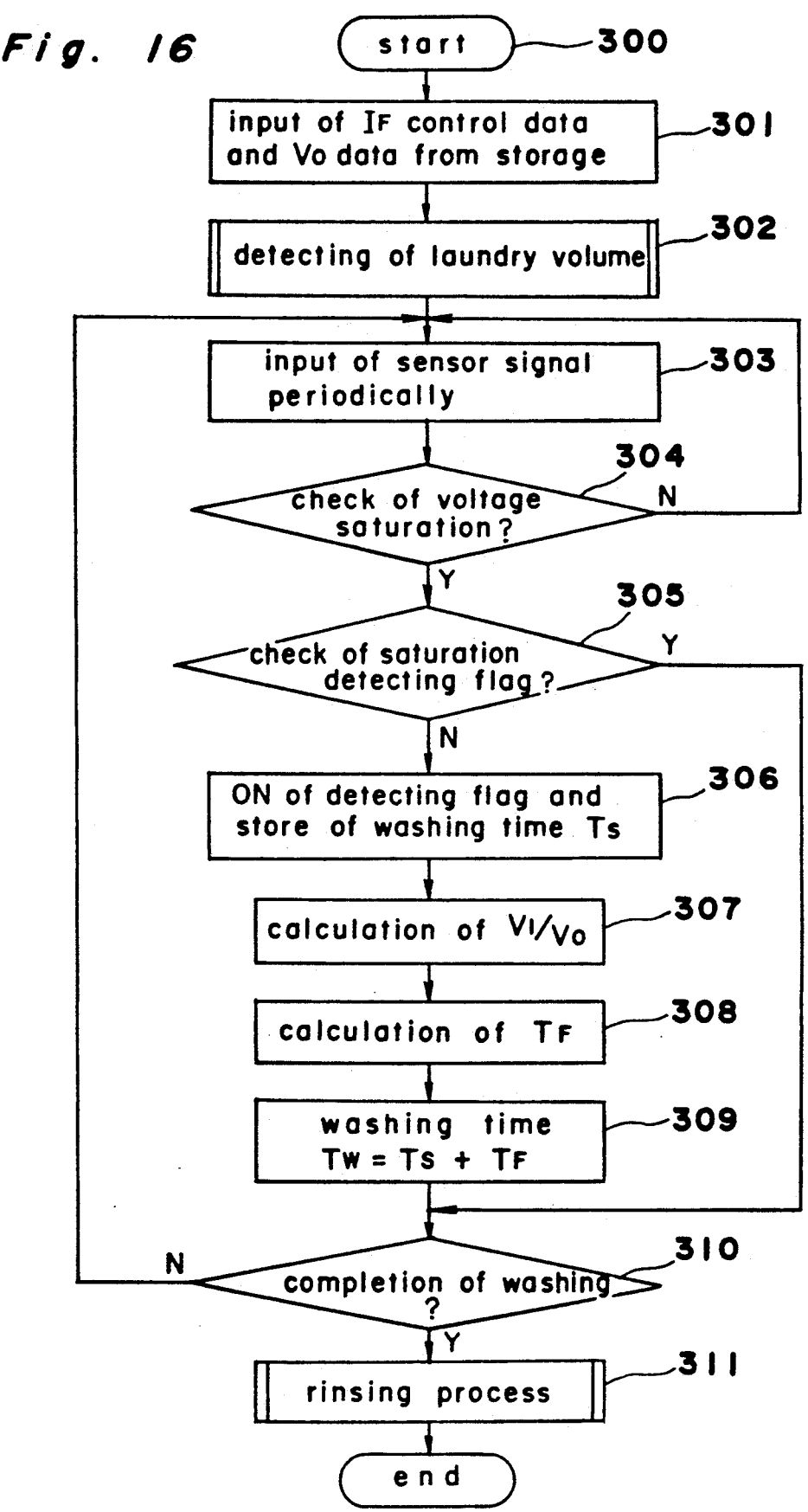
FIG. 16 is a flow chart showing the controlling operation of washing.

The control of washing according to the present embodiment is carried out as shown in FIG. 16.

When washing is started in step 300, IF controlling data stored in the previous rinsing process and the voltage data Vo are read from the storage device in step 301, thus controlling the output of the optical sensor. Step 302 is a volume detecting routine in which the volume of the laundries is detected, and the minimum and maximum washing times are determined in accordance with the detected volume of the laundries. After the start of stirring, the optical sensor is periodically controlled in step 303, generating the sensor output. In step 304, it is detected whether the sensor voltage is saturated to a predetermined value. When the output voltage is saturated, a saturation detecting flag is checked in step 305. Thereafter, the saturating time TS is stored in step 306, and further the changing ratio V1/Vo from the time of clear water (supplied as rinse water into the washer tank) is calculated in step 307. In step 308, TF is obtained based on the graph of FIG. 15. Then, in step 309, the washing time TW is obtained. When the washing time TW is consumed in step 310, the washing process is completed. It is possible to control the washing time to TW=TS+TF+TG in step 309. The time TG is changed corresponding to the volume of laundries. The dirt content is inversely proportional to the logarithmic value of the changing ratio V1/Vo, and accordingly, the optimum washing time can be obtained in accordance with the dirt content.

Figure 17:
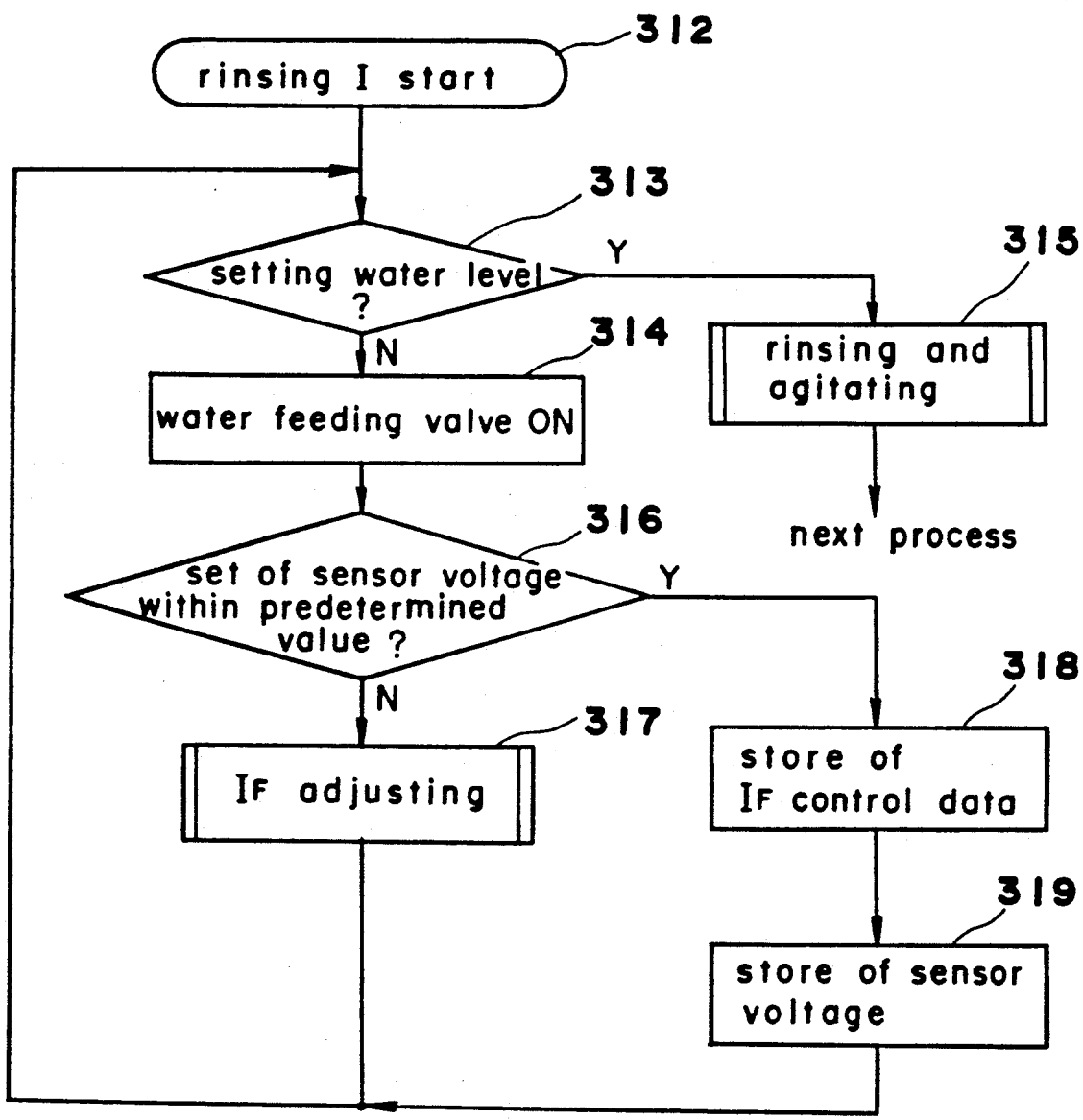
FIG. 17 is a flow chart showing the output controlling operation for the optical sensor.

The output control and storing operations in the rinsing process according to a modified embodiment will be described with reference to FIG. 17.

At the first rinsing time in step 312, the output of the optical sensor is controlled during the supply of rinse water, i.e., before the rinse water is supplied to a set level, so that the output voltage Vo becomes a set value. In step 313, the water level of the supplied rinse water is detected. If the water level is not sufficient, rinse water is fed again in step 314. Then, if the sensor voltage does not reach the set value in step 316, the current IF of the light emitting diode is controlled by PWM signals in step 317. When the sensor voltage reaches the set value, the output controlling data (PWM signal data) and output signals Vo from the sensor are stored in steps 318 and 319, respectively.

In the control of washing described above, even if the laundries are soiled with mud, and accordingly when the saturating time of the sensor voltage becomes short, the washing time can be changed and lengthened in accordance with the dirt content of the laundries (light permeability). Therefore, a large washing and cleansing power is secured. Likewise, when the oily stains are to be washed and therefore the saturating time is long, the washing time can be lengthened. In short, according to the washing machine of the present invention, it is possible to control washing in accordance with the quality and quantity of the dirt. Since the dirt of the laundries in general domestic use is easy to decompose by water and detergent, in such case, it will fit the user's sense to control the washing time in accordance with the changing ratio V1/Vo, with reducing the saturating time. In other words, when the changing ratio is small and the saturating time TS is short, the laundries are judged to be lightly soiled, whereby the washing time is set shorter. On the other hand, when the changing ratio is large, with a small saturating time TS, the laundries are judged to be considerably dirty, and the washing time is set longer. The washing machine of the present invention can realize this type of control.

As is made clear from the foregoing description of preferred embodiments, the washing machine of the present invention is significantly effective as follows:

(1) Since the optical sensor is initialized on the basis of the light permeability of water (clear water) or air supplied into the washer tank, a situation can be prevented in which an output of the optical sensor is erroneously decreased as a result of staining. Therefore, an erroneous detection by the optical sensor is avoided, and an accurate detection of dirt is ensured.

(2) Since the reference value is changed between the water and air, the optical sensor can be initialized both for water and for air.

(3) Since it is so arranged as to detect the dirt of the laundries through detection of the light permeability of the optical sensor after the sensor is initialized, the detection is free from influences of stains to the optical sensor, and accordingly the optical sensor is reliably accurate for a long period of use.

(4) Since the dirt of the laundries is detected on the basis of both the saturating time of the output of the optical sensor and the changing width of the output, the quality and quantity of the dirt can be taken into consideration in control of washing and rinsing.

(5) Since there is provided, in addition to the optical sensor, a volume sensor for detecting the volume of the laundries, control of washing and rinsing can be carried out based on the data of the dirt detected by the optical sensor and the data of the laundry volume detected by the volume sensor. Therefore, control of washing and rinsing can be realized as if by the operator himself or herself.

(6) Since the detergent type is detected through detection of the output from the optical sensor after the optical sensor is initialized at the reference value, the washing machine can utilize a wide variety of detergents.

(7) Since washing and rinsing are controlled corresponding to the detergent type which greatly influences the optical sensor in detection of the light permeability, a highly accurate control is gained.

(8) Since the data of the kind of detergent type, data of the laundry volume and dirt content data from the optical sensor are all together utilized for control, washing and rinsing can be controlled with a much higher accuracy.

Although the present invention has been fully described by way of example with reference to the preferred embodiments thereof, it is to be noted here that various changes and modifications would be apparent to those skilled in the art. Such changes and modifications are to be understood as defined by the appended claims unless they depart therefrom.

What is claimed is:

1. A washing machine comprising:
an optical sensor means for detecting a light permeability of a liquid in a washer tank, said optical sensor means including a light emitting element for emitting light and a light receiving element for detecting the light emitted from said light emitting element;

an output control means for varying a luminous intensity of the light emitted from said light emitting element;

a memory means for storing at least one predetermined reference value; and, a control means for controlling process cycles of the washing machine in accordance with the light permeability detected by said optical sensor means;

wherein said output control means includes means for increasing the luminous intensity of the light emitted from said light emitting element such that an intensity of light detected by said light receiving element is equal to or greater than the predetermined reference value stored in said memory means during at least one of two operating states, a first of the two operating states being a state in which liquid is absent from the water tank and a second of the two operating states being a state in which liquid is present in the water tank and prior to agitation of the liquid in the water tank.

2. A washing machine as recited in claim 1, further comprising a liquid level detecting means for detecting a liquid level within the washer tank, wherein the at least one predetermined reference value stored in said memory means includes a first reference value and a second reference value, wherein said output control means sets the luminous intensity of the light emitted from said light emitting element in accordance with the first reference value when the liquid level detected by said liquid level detecting means is below a predetermined level, and wherein said output control means sets the luminous intensity of the light emitted from said light emitting element in accordance with the second reference value when the liquid level detected by said liquid level detecting means is above the predetermined level.

3. A washing machine as recited in claim 1, further comprising a level detecting means for detecting a liquid level within the washer tank, wherein said output control means sets the luminous intensity of the light emitted from said light emitting element when the liquid level detected by said level detecting means is not lower than a predetermined level.

4. A washing machine as recited in claim 1, wherein said memory means further includes means for storing data corresponding to the intensity of light detected by said light detecting element.

5. A washing machine as recited in claim 4, wherein said output control means includes means for accessing the data stored in said memory means when setting the luminous intensity of the light emitted from said light emitting element.

* * * * *